United States Patent
Gajda et al.

(10) Patent No.: US 7,205,448 B2
(45) Date of Patent: Apr. 17, 2007

(54) PROCESS FOR THE REMOVAL OF NITROGEN COMPOUNDS FROM A FLUID STREAM

(75) Inventors: Gregory J. Gajda, Mount Prospect, IL (US); Guy B. Woodle, Mount Prospect, IL (US); Deng-Yang Jan, Elk Grove Village, IL (US); Andrew S. Zarchy, Kildeer, IL (US)

(73) Assignee: UOP LLC, Des Plaines, IL (US)

( * ) Notice: Subject to any disclaimer, the term of this patent is extended or adjusted under 35 U.S.C. 154(b) by 381 days.

(21) Appl. No.: 10/740,872

(22) Filed: Dec. 19, 2003

(65) Prior Publication Data

US 2005/0137442 A1 Jun. 23, 2005

(51) Int. Cl.
*C07C 7/12* (2006.01)
*C10G 25/00* (2006.01)

(52) U.S. Cl. ............. 585/823; 585/448; 585/820; 585/822; 585/833; 208/247; 208/254 R; 208/299; 208/300; 208/301; 502/66

(58) Field of Classification Search ............ 208/254 R, 208/301, 247, 299, 300; 502/66; 585/448, 585/823, 820, 822, 833
See application file for complete search history.

(56) References Cited

U.S. PATENT DOCUMENTS

| | | | |
|---|---|---|---|
| 2,999,861 A | 9/1961 | Fleck et al. ............ 260/290 |
| 4,107,224 A | 8/1978 | Dwyer ............ 260/671 R |
| 4,185,040 A | 1/1980 | Ward et al. ............ 585/467 |
| 4,310,440 A | 1/1982 | Wilson et al. ............ 252/435 |
| 4,440,871 A | 4/1984 | Lok et al. ............ 502/214 |
| 4,567,029 A | 1/1986 | Wilson et al. ............ 423/306 |
| 4,774,377 A | 9/1988 | Barger et al. ............ 585/323 |
| 4,846,962 A | 7/1989 | Yao ............ 208/301 |
| 4,891,458 A | 1/1990 | Innes et al. ............ 585/323 |
| 5,030,786 A | 7/1991 | Shamshoum et al. ............ 585/467 |
| 5,220,099 A | 6/1993 | Schreiner et al. ............ 585/820 |
| 5,271,835 A | 12/1993 | Gorawara et al. ............ 208/228 |
| 5,723,710 A | 3/1998 | Gajda et al. ............ 585/467 |
| 5,744,686 A | 4/1998 | Gajda ............ 585/823 |
| 5,880,052 A * | 3/1999 | Ramirez de Agudelo et al. ............ 502/66 |
| 5,942,650 A | 8/1999 | Gajda ............ 585/448 |
| 6,019,887 A | 2/2000 | Ramirez de Agudelo ............ 208/254 R |
| 6,107,535 A | 8/2000 | Rossini et al. ............ 585/823 |
| 6,617,482 B1 | 9/2003 | Venkat et al. ............ 585/448 |

FOREIGN PATENT DOCUMENTS

| | | |
|---|---|---|
| EP | 0 922 020 B1 | 5/2002 |
| WO | WO 93/00992 | 1/1993 |
| WO | WO 00/35836 | 6/2000 |
| WO | WO 01/07383 | 2/2001 |

OTHER PUBLICATIONS

Donald W. Breck, Zeolite Molecular Sieves, 1974, John Wiley & Sons, Inc., New York (pp. 45-58).

* cited by examiner

*Primary Examiner*—Glenn Caldarola
*Assistant Examiner*—Prem C. Singh
(74) *Attorney, Agent, or Firm*—James C. Paschall

(57) ABSTRACT

At lower temperatures an acidic molecular sieve adsorbent preferentially adsorbs water and basic organic nitrogen compounds over weakly basic organic nitrogen compounds such as nitrites. Elevated temperatures improve the capacity of acidic molecular sieve adsorbents to adsorb nitrites in the presence of water.

16 Claims, No Drawings

US 7,205,448 B2

PROCESS FOR THE REMOVAL OF NITROGEN COMPOUNDS FROM A FLUID STREAM

FIELD OF THE INVENTION

This invention relates to a process for removing nitrogen compounds from a fluid stream. More particularly, this invention relates to the use of a selective adsorption process for removing nitrites from a hydrocarbon stream.

BACKGROUND OF THE INVENTION

The use of molecular sieves as catalysts in aromatic conversion processes are well known in the chemical processing and refining industry. Aromatic conversion reactions of considerable commercial importance include the alkylation of aromatic compounds such as in the production of ethyltoluene, xylene, ethylbenzene, cumene, or higher alkyl aromatics and in disproportionation reactions such as toluene disproportionation, xylene isomerization, or the transalkylation of polyalkylbenzenes to monoalkylbenzenes. Often the feedstock to such an aromatic conversion process will include an aromatic component or alkylation substrate, such as benzene, and a $C_2$ to $C_{20}$ olefin alkylating agent or a polyalkyl aromatic hydrocarbon transalkylating agent. In the alkylation zone, the aromatic feed stream and the olefinic feed stream are reacted over an alkylation catalyst to produce alkylated benzene such as ethylbenzene or cumene. Polyalkylated benzenes are separated from monoalkylated benzene product and recycled to a transalkylation zone and contacted with benzene over a transalkylation catalyst to yield monoalkylated benzenes and benzene.

The catalysts for such alkylation or transalkylation reactions generally comprise zeolitic molecular sieves. U.S. Pat. No. 4,891,458 discloses the presence of a catalyst comprising zeolite beta. U.S. Pat. No. 5,030,786 discloses an aromatic conversion process employing zeolite Y, zeolite omega and zeolite beta molecular sieve catalyst. U.S. Pat. No. 4,185,040 discloses the alkylation of benzene to produce ethylbenzene or cumene employing zeolites such as molecular sieves of the X, Y, L, B, ZSM-5 and Omega crystal types. U.S. Pat. No. 4,774,377, discloses an aromatic conversion process involving alkylation over a catalyst comprising a solid phosphoric acid component followed by transalkylation using aluminosilicate molecular sieve transalkylation catalysts including X, Y, ultrastable Y, L, Omega, and mordenite zeolites.

Water is often found in the aromatic feedstock to alkylation and transalkylation reactions, especially in benzene feed. Benzene feed is often water saturated, for example, when it is recycled from a styrene monomer unit. Molecular sieve catalysts employed in alkylation reactions in the vapor or the liquid phase may be sensitive to water at various levels or sulfur compounds in the feedstock. U.S. Pat. No. 4,107,224 discloses that water and hydrogen sulfide in vapor phase reactions may be tolerable if more rapid aging of the catalyst is acceptable. U.S. Pat. No. 5,030,786 disclose the dehydration of the feedstock to a water content of no more than 100 ppm, and preferably 50 ppm or less when the reaction zone is operated to maintain the reactor contents in the liquid phase. However, WO 93/00992 discloses that in the starting phase the zeolite catalyst for alkylation or transalkylation processes should have a minimum water content of more than 3.5 wt-%, related to catalyst composition. EP 0 922 020 B1 discloses uses of a solid acid to adsorb impurities from a benzene alkylation feed which is dried to contain no more than 200 ppm water at a temperature of between 130° and 300° C. to improve the lifetime of a zeolitic alkylation or transalkylation catalyst.

Other impurities present in the feedstock to an aromatic conversion reactor, particularly basic impurities such as basic organic nitrogen compounds (ONCs), neutralize the solid acids that comprise most present day aromatic alkylation catalysts. Catalyst performance and the catalyst life are adversely affected. Even very low nitrogen concentrations in the feed increase the catalyst regeneration frequency during which accumulated nitrogen compounds and coke must be combusted from the catalyst. As more active zeolite catalysts are employed in aromatic conversion reactions, the degradation of catalyst life by nitrogen impurities in the feedstock must be more carefully controlled. Processes are sought to reduce the impact of nitrogen impurities on the catalyst in the reaction zone. Basic nitrogen compounds that degrade catalyst life include indoles, pyridines, quinolines, diethanol amine (DEA), morpholines including N-formyl-morpholine (NFM) and N-methyl-pyrrolidone (NMP). NFM and NMP are used as aromatic extraction agents and DEA is a corrosion inhibitor that all often contaminate aromatic feed streams. U.S. Pat. No. 5,220,099 teaches removing indole, quinoline and pyridine impurities with zeolites and using toluene with dissolved water to desorb the impurities from the zeolites. WO 00/35836 discloses contacting an alkylated benzene with molecular sieve to remove catalyst poisons including nitrogen compounds prior to feeding it to a transalkylation reactor. WO 01/07383 discloses contacting a feed stream to an alkylation zone with a zeolite to remove organically bound nitrogen. U.S. Pat. No. 4,846,962 discloses contacting a solvent extracted oil with an amorphous silica-alumina or crystalline zeolite adsorbent to remove basic nitrogen compounds such as NMP. The adsorbent may contain up to 30 wt-% water.

U.S. Pat. No. 5,271,835 discloses the presence of polar impurities in the $C_3$ to $C_5$ product fraction from a fluid catalytic cracking unit. The impurities were found to include weakly basic ONCs such as acetonitrile. Acrylonitriles and propionitrile can also be found in hydrocarbon streams that may serve as feed to an aromatic alkylation process. These polar compounds are attracted to and poison the catalyst used in aromatics alkylation processes. U.S. Pat. No. 6,019,887 teaches using a cationic nonacidic zeolite at no more than 300° C., and U.S. Pat. No. 6,107,535 teaches using silica gel to adsorb nitriles at room temperature from a hydrocarbon stream. U.S. Pat. No. 2,999,861 teaches using an X zeolite to selectively adsorb basic ONCs over weakly basic ONCs including nitriles, nitrates and nitro compounds at −18 to 427° C. U.S. Pat. No. 5,744,686 and U.S. Pat. No. 5,942,650 teach removing water from a benzene stream containing nitriles before removing the nitriles by contacting the benzene stream with nonacidic molecular sieves at −18° to 204° C. U.S. Pat. No. 6,617,482 B1 teaches higher silica zeolites are more effective when water is present. However, only adsorption of NFM in the presence of water is demonstrated at room temperature; adsorption of nitriles is demonstrated only in the absence of water in this reference. Low concentrations of nitrites in the ranges of parts per million and parts per billion can cumulatively deactivate alkylation catalysts faster than other deactivation mechanisms such as coking.

Clay or resin guard beds are inexpensive means to adsorb ONCs from aromatic alkylation feed streams. During adsorption of organic nitrogen from alkylation feed streams, coke also forms on the adsorbents. These adsorbents become spent when all of the adsorption sites are occupied by either ONCs or coke. Spent clay and resin guard beds cannot be regenerated by combustion. Guard beds containing molecular sieves can be regenerated by combusting both ONCs and coke off of the adsorbent.

An object of the invention is to provide a guard bed that will adsorb nitrites from a hydrocarbon feed stream.

A further object of the invention is to provide a guard bed that will adsorb nitrites from a hydrocarbon feed stream in the presence of water.

SUMMARY OF THE INVENTION

We have found that conventional adsorbents such as clay and resin materials do not sufficiently adsorb nitrites from hydrocarbon streams in the presence of water. We have further found at lower temperatures an acidic molecular sieve adsorbent preferentially adsorbs water and basic ONCs over weakly basic ONCs such as nitrites in hydrocarbon streams. However, elevated temperatures improve the capacity of acidic molecular sieve adsorbents to adsorb nitrites in the presence of water. It is hypothesized that the acidic molecular sieves serve as a catalyst at the elevated temperature to hydrolyze the nitrile to an amine or an amide. The basic amine or amide is then strongly adsorbed on the acidic molecular sieve. The molecular sieve may be regenerated when spent. We have also discovered that the presence of water also mitigates accumulation of coke on the adsorbent, thereby prolonging the regeneration cycles.

DETAILED DESCRIPTION OF THE INVENTION

The hydrocarbon feed stream of this invention is generally a liquid and may comprise from about 30 wppb to about 1 mol-% ONCs and typically 100 wppb to 100 wppm ONCs. The present invention is demonstrated to be capable of adsorbing ONCs present in concentrations in the parts per million range and we believe it can effectively nullify the effect ONC concentrations in the parts per billion range on downstream catalysts. The hydrocarbon stream may contain water up to and beyond saturation conditions. The hydrocarbon feed stream containing the ONCs and water may be an aromatic feed stream preferably including benzene and is suitably predominantly benzene. The aromatic hydrocarbon feed stream will typically include no more than 1.0 wt-% olefins when it is run through an adsorbent bed.

ONCs typically include a larger proportion of basic ONCs such as indoles, pyridines, quinolines, diethanol amine (DEA), morpholines including N-formyl-morpholine (NFM) and N-methyl-pyrrolidone (NMP). ONCs also may include to a lesser proportion weakly basic nitrites, such as acetonitrile, propionitrile, acrylonitrile, and mixtures thereof. The basic ONCs are adsorbed well on conventional clay or resin adsorbent guard beds. The hydrocarbon feed stream is charged to such a conventional, impurity adsorption zone to adsorb basic ONCs and other impurities and provide a treated adsorption effluent, depleted in basic ONCs. We have found that weakly basic ONCs such as nitriles do not adsorb well on conventional resin and clay adsorbents. The nitrites get through the conventional adsorbent bed and may adversely impact downstream processing, such as an alkylation or transalkylation reaction zone.

Clay adsorbents for removing basic ONCs include clays provided by Sudchemie such as SC 630G, SC 636G and the preferred SC 626 GS. F-24 clay provided by Filtrol Corp. is also suitable. Resin adsorbents for removing basic ONCs include the Amberlyst line of resins, A-15 being preferred and available from Rohm & Haas Company, and resins such as CT-175 provided by Purolite International Limited. Other types of clay and resin adsorbents may be suitable. The clay or resin adsorber can be run at conditions sufficient to keep the aromatic stream at least partially in the liquid phase. Ambient temperature up to 38° C. (100° F.) and pressures just above atmospheric up to 206 kPa (30 psia) should be sufficient. Clays and resins capacity ranges typically between 6 and 10 wt-% amines and 1 and 2 wt-% NFM and NMP based on the weight of the adsorbent. However, under these conditions, clay and resin will preferentially adsorb water and NFM and NMP over nitrites. Hence, other measures must be taken to adsorb the nitrites.

Adsorbents of the present invention suited for the removal of weakly basic ONCs include acidic molecular sieves such as the various forms of silicoaluminophosphates, and aluminophosphates disclosed in U.S. Pat. No. 4,440,871; U.S. Pat. No. 4,310,440 and U.S. Pat. No. 4,567,029 as well as zeolitic molecular sieves. As used herein, the term "molecular sieve" is defined as a class of adsorptive desiccants which are highly crystalline in nature, with crystallograpically defined microporosity or channels, distinct from materials such as gamma-alumina. Preferred types of molecular sieves within this class of crystalline adsorbents are aluminosilicate materials commonly known as zeolites. The term "zeolite" in general refers to a group of naturally occurring and synthetic hydrated metal aluminosilicates, many of which are crystalline in structure. Zeolitic molecular sieves in the calcined form may be represented by the general formula:

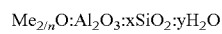

$$Me_{2/n}O:Al_2O_3:xSiO_2:yH_2O$$

where Me is a cation, x has a value from about 2 to infinity, n is the cation valence and y has a value of from about 2 to 10. Typical well-known zeolites that may be used include chabazite, also referred to as Zeolite D, clinoptilolite, erionite, faujasite, Zeolite Beta (BEA), Zeolite Omega, Zeolite X, Zeolite Y, MFI zeolite, Zeolite MCM-22 (MWW), ferrierite, mordenite, Zeolite A, and Zeolite P. Detailed descriptions of some of the above-identified zeolites may be found in D. W. Breck, ZEOLITE MOLECULAR SIEVES, John Wiley and Sons, New York, 1974.

Significant differences exist between the various synthetic and natural materials in chemical composition, crystal structure and physical properties such as X-ray powder diffraction patterns. The molecular sieves occur as agglomerates of fine crystals or are synthesized as fine powders and are preferably tableted or pelletized for large-scale adsorption uses. Pelletizing methods are known which are very satisfactory because the sorptive character of the molecular sieve, both with regard to selectivity and capacity, remains essentially unchanged. Preferred adsorbents include a Zeolite Y and Zeolite X having an alumina or silica binder and a beta zeolite having an alumina or silica binder. Zeolite Y is the most preferred.

In an embodiment, the molecular sieve will usually be used in combination with a refractory inorganic oxide binder. Binders may include either alumina or silica with the former preferred and gamma-alumina, eta-aluminum and mixtures thereof being particularly preferred. The molecular sieve may be present in a range of from 5 to 99 wt-% of the adsorbent and the refractory inorganic oxide may be present in a range of from 1 to 95 wt-%. In an embodiment, the molecular sieve will be present in an amount of at least 50 wt-% of the adsorbent and more preferably in an amount of at least 70 wt-% of the adsorbent.

The molecular sieve in the adsorbent of the present invention is acidic. Using silicon to aluminum ratio as a gauge for acidity level, the silicon to aluminum ratio should be no more than 100 in an embodiment and no more than 25 in a further embodiment. Cations on the molecular sieve are not desirable. Hence, acid washing may be desirable to remove alkali metals such as sodium in the case of Zeolite Y and Beta Zeolite to reveal more acid sites, thereby increasing the adsorptive capacity. Aluminum migrating out of the framework into the binder should also be avoided because it reduces acidity. Incorporation of some level of cations such as alkali earth and rare earth elements into Zeolite X or Y will improve the thermal and hydrothermal stability of the framework aluminum, minimizing the amount of framework aluminum migrating out of the framework. The level of incorporation of the cations should be sufficiently low to avoid inhibiting adsorption performance. The molecular sieve adsorbent of the present invention may have the same composition as the alkylation catalyst in a downstream reactor, such as an alkylation or transalkylation unit. However, when the alkylation catalyst is more expensive than the molecular sieve adsorbent, the composition of the alkylation catalyst and the molecular sieve are preferably different.

As indicated, the presence of water adversely affects adsorption of nitrites on acidic molecular sieves at ambient temperatures. On the surface, it would appear that minimizing the amount of water in the feed to a molecular sieve guard bed would be beneficial. The water would compete with the ONCs for adsorption sites, thereby reducing the capacity of the molecular sieve for ONCs. We have confirmed at lower temperatures that water preferentially adsorbs on acidic molecular sieves over nitrites. However, we further found that in the presence of an inexcessive concentration of water, acidic molecular sieves adsorb a greater concentration of nitrites at higher temperatures. Although not wishing to be bound by any particular theory, we believe the nitrites are insufficiently basic to adsorb onto the acidic molecular sieve adsorbent. However, in the presence of water, the nitrites catalytically hydrolyze to amides or amines over the acidic molecular sieve. The basic amides or amines then adsorb onto the acidic molecular sieve.

The contaminated hydrocarbon feed stream to be purified of nitriles should be run through a nitrogen adsorption zone of acidic molecular sieve in the presence of water at an elevated temperature in an embodiment of at least about 120° C. and no more than about 300° C., in an embodiment, in the range of greater than about 125° C. and no more than about 300° C., and in a further embodiment, in the range of about 150° C. to about 200° C. The pressure in the adsorbent bed should be in the range of about 34.5 kPa to about 4136.9 kPa (gauge) (5 to 600 psig). The ONC loading on the molecular sieve adsorbent may reach from about 0.6 to about 1.0 wt-% before regeneration is needed. The ONC loading on clay adsorbent is about 1.5 to about 6.0 wt-% and the ONC loading on resin adsorbent is about twice that of clay. Because the resin or clay adsorbent has a greater adsorption capacity for ONCs and is less expensive, the impure hydrocarbon stream may be run through a conventional clay or resin guard bed to remove the basic ONCs before it is delivered to the acidic molecular sieve guard bed to remove the nitrites. However, the acidic molecular sieve guard bed will adsorb basic ONCs that survive the conventional adsorbent bed. It may be preferable to install the acidic molecular sieve adsorbent bed in downstream communication with the conventional adsorbent bed. Hence, at least a portion of the effluent from the conventional adsorbent bed should eventually feed the acidic molecular sieve adsorbent bed. Moreover, because the temperature of the effluent from the conventional adsorbent bed may be ambient, a heat exchanger may be situated in downstream communication with the conventional adsorbent bed and in upstream communication with the hot adsorbent bed to adjust the temperature suitably for the hot adsorbent bed. Hence, at least a portion of the effluent from the conventional adsorbent bed will be heated or cooled in the heat exchanger and at least a portion of the effluent from the heat exchanger will feed to the hot adsorbent bed. In an embodiment, all of the alkylation substrate stream should be denitrogenated in the hot adsorbent bed before it is fed to an alkylation and/or transalkylation reaction zone.

The water concentration of the hydrocarbon feed stream should be between about 20 wppm to about 500 wppm and preferably between 50 wppm and 150 wppm while in the molecular sieve guard bed. In an embodiment, the water concentration should be stoichiometric with respect to the conversion of nitrile to amines or amides.

We have also found that the presence of water in the molecular sieve guard bed reduces coke formation on the adsorbents at elevated temperatures. Coke accumulation on acid sites of the molecular sieve serves to block adsorption of ONCs, resulting in shorter cycles between regeneration. However, by alleviating the coke formation on the acid sites, the molecular sieve guard bed can maintain longer cycles between regeneration and maintain maximum adsorption capacity over multiple cycles of operation because each regeneration cycle will require significantly less severity.

The conventional clay or resin guard bed cannot be regenerated when spent. Instead, the spent clay or resin must be disposed. Spent molecular sieve of the present invention may be regenerated. The molecular sieve guard bed may contain one or more fixed beds of molecular sieve. As the capacity of the on-stream molecular sieve adsorption bed is reached; that is, preferably before a substantial portion of the ONCs have passed through the on-stream adsorption bed, the feed stream is directed to a stand-by molecular sieve adsorption bed in the adsorption zone. The formerly on-stream adsorption bed may then be drained by passing the contents to a fractionation zone. Otherwise, the process is stopped during regeneration of the adsorbent bed. The adsorption bed may be regenerated with a hot natural gas stream or by a carbon bum to combust the ONCs from the molecular sieve or by any other conventional method. The regenerated adsorption bed is then placed on stand-by until the on-stream adsorption bed reaches capacity.

In the selective alkylation of aromatics by an olefinic alkylation agent as catalyzed by an acidic catalyst, the olefins may contain from 2 up to at least 20 carbon atoms, and may be branched or linear olefins, either terminal or internal olefins. Thus, the specific nature of the olefin is not particularly important. What the alkylation reactions share in common is that the reactions are conducted under at least partially liquid phase conditions, a criterion readily achieved for the lower members by adjusting reaction pressures. Among the lower olefins, ethylene and propylene are the most important representatives. An olefinic feed stream comprising an alkylation agent may include ethylene and/or propylene. An olefinic feed stream comprising propylene will be at least 65 wt-% pure with the balance including a large proportion of propane, with some propylene feeds being over 99 wt-% pure. Ethylene feeds will typically be over 99 wt-% pure. Among the remaining olefins, the class of detergent range olefins is of particular interest. This class consists of linear olefins containing from 6 up through about 20 carbon atoms which have either internal or terminal unsaturation. Linear olefins containing from 8 to 16 carbon atoms are particularly useful as detergent range olefins, and those containing from 10 up to about 14 carbon atoms are especially preferred for detergent range olefins. Alkylation agents may also be provided by alkyl constituents of a polyalkylbenzene in a transalkylation reaction zone. Diethylbenzene, triethylbenzene and diisopropylbenzene are prominent examples of polyalkylbenzenes that can provide such alkylation agents.

Benzene is by far the most important representative of the alkylatable aromatic compounds which may be used as an alkylation substrate in the practice of the invention. An aromatic feed stream may comprise from about 5 to 99.9 mol-% benzene and may be a recycle stream from a styrene monomer production plant. More generally the aromatic compounds may be selected from the group consisting of benzene, naphthalene, anthracene, phenanthrene, and substituted derivatives thereof. The most important class of substituents found on the aromatic nucleus of alkylatable aromatic compounds are alkyl moieties containing from 1 up to about 20 carbon atoms. Another important substituents is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, and so forth; phenol, cresol, anisole, ethoxy-, propoxy-, butoxy-, pentoxy-, hexoxybenzene, and so forth.

A wide variety of catalysts can be used in the alkylation reaction zone. Suitable catalysts for use in the reaction zone will comprise any catalyst that does not suffer deleterious effects from the presence of water. Preferably, a substantial quantity of water may be tolerated or desired in the presence of the alkylation catalyst. A substantial quantity of water preferably means a water concentration in the reactants entering the alkylation zone of at least 50 wppm. The alkylation reaction zone may have a water content of as little as 20 wppm, to over 200 wppm and up to 1000 wppm or more. The preferred catalyst for use in this invention is a zeolitic catalyst. The catalyst of this invention will usually be used in combination with a refractory inorganic oxide binder. Preferred binders are alumina or silica. Suitable zeolites include zeolite beta, ZSM-5, PSH-3, MCM-22, MCM-36, MCM-49, and MCM-56. Zeolite beta is described in U.S. Pat. No. 5,723,710. Preferred alkylation catalysts are a type Y zeolite having an alumina or silica binder or a beta zeolite having an alumina or silica binder. The zeolite will be present in an amount of at least 50 wt-% of the catalyst and more preferably in an amount of at least 70 wt-% of the catalyst.

The particular conditions under which the alkylation reaction is conducted depends upon the aromatic compound and the olefin used. Since the reaction is conducted under at least partial liquid phase conditions, reaction pressure is adjusted to maintain the olefin at least partially in the liquid phase. For higher olefins the reaction may be conducted at autogenous pressure. Pressures can vary within a wide range of about 101 kPa to about 13172 kPa. As a practical matter the pressure normally is in the range between about 1379 kPa and about 6985 kPa (200 to 1000 psig) but usually is in a range between about 2069 and 4137 kPa (300 and 600 psig). But we emphasize again that pressure is not a critical variable and needs to be sufficient only to maintain at least partial liquid phase conditions. Representative alkylation temperatures include a range of between 170° and 250° C. for alkylation of benzene with ethylene and temperatures of 90° to 160° C. for the alkylation of benzene by propylene. The temperature range appropriate for alkylation of the alkylatable aromatic compounds of our invention with the olefins in the $C_2$ to $C_{20}$ range is between about 60° and about 400° C., with the most usual temperature range being between about 90° and 250° C. Reactants generally pass through the alkylation zone at a mass flow rate sufficient to yield a liquid hourly space velocity from 0.2 to 50 $hr^{-1}$ and especially from about 0.5 to 10 $hr^{-1}$.

The ratio of alkylatable aromatic compound to olefin used in the process of the invention will depend upon the degree of selective alkylation desired as well as the relative costs of the aromatic and olefinic components of the reaction mixture. For alkylation of benzene by propylene, benzene-to-olefin ratios may be as low as about 1.5 and as high as about 10.0, with a ratio of 2.0 to 8.0 being preferred. Where benzene is alkylated with ethylene, a benzene-to-olefin ratio between about 2:1 and 8:1 is preferred. For detergent range olefins of $C_6$ to $C_{20}$, a benzene-to-olefin ratio of between 5:1 up to as high as 30:1 is generally sufficient to ensure the desired alkylation selectivity, with a range between about 8:1 and about 20:1 even more highly desired.

In the production of cumene with a benzene alkylation substrate and a propylene alkylating agent, the propylene-containing stream will typically also contain propane. The propylene stream may contain from 0 to 50 wt-% propane, and typically, the propylene stream contains from 0.5 to 35 wt-% propane.

The alkylation reaction zone will often provide a wide variety of undesired by-products. For example, in the alkylation of benzene with ethylene to produce ethylbenzene, the reaction zone can also produce di- and triethylbenzene in addition to other ethylene condensation products. Similarly, in the alkylation of benzene with propylene to produce cumene, the reaction zone can produce di- and triisopropylbenzene in addition to still more condensation products. These polyalkylated aromatics contact additional aromatic substrate in a transalkylation reactor to produce additional monoalkylated product. The transalkylation reaction zone of this invention will use a zeolitic catalyst. The zeolite will be present in an amount of at least 50 wt-% of the catalyst and more preferably in an amount of at least 90 wt-% of the catalyst. In most cases the zeolitic catalyst again includes an inorganic oxide binder. The preferred inorganic oxide for use in the transalkylation catalyst is alumina with gamma-alumina, eta-aluminum and mixtures thereof being particularly preferred. The zeolite may be present in a range of from 5 to 99 wt-% of the catalyst and the refractory inorganic oxide may be present in a range of from 1 to 95 wt-%. Preferred transalkylation catalysts are a type Y zeolite having an alumina or silica binder or a beta zeolite having an alumina or silica binder.

There is no requirement that the alkylation reaction zone and the transalkylation reaction zone use the same catalyst. This process is useful for any arrangement of alkylation reaction zone and transalkylation reaction. However, it has been found that a beta zeolite or a high Y type zeolite contained in an alumina binder will perform very well when used in both the alkylation reaction zone and the transalkylation reaction zone. Therefore, in the preferred embodiment of this invention, in the cumene context, both reaction zones will use the same catalyst, beta zeolite. Whereas, in the case of ethylbenzene, the alkylation and transalkylation zones will preferably use beta zeolite and Y-type zeolite, respectively. Additionally, transalkylation reactions occur in an alkylation reaction zone and alkylation reactions occur in a transalkylation reaction zone, both zones may be referred to as alkylation zones.

It may be desirable to use a first bed of an alkylation zone or transalkylation zone that uses an acidic molecular sieve catalyst as an adsorbent zone for the removal of nitrites. In such an event, the adsorbent and the catalyst should be spaced apart. The alkylation agent should bypass the adsorption zone and be delivered to an interbed space to mix with the denitrogenated alkylation substrate exiting the adsorption zone. However, it may be preferable to contain the hot adsorption zone and the alkylation zone in separate vessels.

The transalkylation reaction can be carried out in a broad range of operating conditions that include a temperature of from 100° to 390° C. (212° to 734° F.) and pressure ranging from 101 to about 13171 kPa (14.7 to 1910 psia). Again, the pressure would generally be selected so that the reactants will remain in the liquid phase. Accordingly, preferred pressures for the transalkylation reaction zone range from 1013 to about 5066 kPa (147 to 734 psia). A liquid hourly space velocity of from 0.2 to 50 $hr^{-1}$ is desirable for the transalkylation reaction zone with LHSV of from 0.5 to 5 $hr^{-1}$ being preferred.

The transalkylation and alkylation reaction zones may be operated and arranged in any manner that provides the desired operating temperatures and number of contacting stages. Multiple contacting stages in the alkylation zone are routinely used to provide cooling by staged addition of reactants to multiple beds of alkylation catalyst. The multiple injection of the reactants serves to cool the stages between alkylation catalyst beds and provide temperature control. The alkylation catalyst is ordinarily arranged in multiple beds to permit interbed injection of alkylating agent. The separate alkylation catalyst beds may be arranged in a single vessel or in multiple vessels. This invention can be used with a traditional parallel arrangement for the alkylation zone and the transalkylation zone where feed streams are sent independently to each reaction zone and the effluent separately recovered. Alternatively, the reaction zone may have a series flow arrangement with the effluent from the transalkylation zone cascading to the alkylation zone along with additional benzene or vice versa. In the alkylation zone, a large excess of benzene may pass through a series of alkylation catalyst beds with interstage injection of alkylating agent and any additional quantities of benzene. Alkylation reactor effluent recycle may also be used advantageously to quench individual catalyst beds for further improvement in temperature control without the need for additional consumption of fresh benzene. In the series flow arrangement a common vessel may contain a transalkylation reaction zone and one or more alkylation reaction zones. For very large units, separate vessels for the transalkylation catalyst bed and one or more of the alkylation catalyst beds may be more advantageous.

A separation zone will be used to recover alkylate product. An overhead condenser on at least one fractionation column in a separation zone may be used for the separation of water from an overhead stream and the return of a portion of the aromatic hydrocarbon condensate to the column as reflux. Removal of water from the overhead is difficult due to the high solubility of water in benzene. However, some water in the benzene stream facilitates the removal of nitriles. The overhead condenser of a benzene column may be operated to reduce the water concentration to a level of about 500 wppm. An intermediate stream from a depropanizer column may provide a benzene stream with a water concentration of 50 to 150 wppm.

The invention will be further clarified by a consideration of the following examples, which are intended to be purely exemplary of the use of the invention.

EXAMPLES

Example I

A test was run to determine the effectiveness of an acidic molecular sieve in adsorbing acetonitrile from a benzene stream containing water at low temperatures. The adsorbent was prepared by extruding approximately 80 wt-% Y-zeolite with about 20 wt-% alumina binder. After drying the adsorbent was crushed and particles between 20 and 40 mesh were loaded into eight vessels fluidly communicated in series. Benzene feed saturated with water, which is about 500 wppm water, and loaded with 1 wppm acetonitrile was run through the eight adsorbent vessels in series at ambient temperature and pressure.

The ultimate loading in terms of adsorbed nitrogen relative to the adsorbent averaged over the eight adsorbent beds was 0.125 wt-%. The adsorbent in the first five beds had adsorbed its capacity, allowing acetonitrile through the bed, within one day and the adsorbent in beds six through eight adsorbed its capacity within two days.

Adsorbent from the beds was then rinsed with water at 50° C. for an hour. Ninety-seven percent of the nitrogen was extracted from the adsorbent. Hence, at lower temperatures water impairs the adsorption of acetonitrile and/or is adsorbed preferentially to acetonitrile.

Example II

A series of test were conducted to compare the adsorption performance of clay, resin and molecular sieve adsorbents for acetonitrile, NMP and NFM. The adsorbents were loaded into eight vessels fluidly communicated in series. Toluene feed saturated with water, which is about 500 wppm water, and target loaded with 1 wppm each of acetonitrile, NFM and NMP was run through the eight adsorbent vessels in series at ambient temperature and pressure. A toluene feed for one experiment was without water. The Y zeolite was prepared by extruding approximately 80 wt-% Y-zeolite with about 20 wt-% alumina binder.

Table I compares the time it takes for organic nitrogen impurities to break through the selected adsorbent beds.

TABLE I

| | Adsorbent | | | |
|---|---|---|---|---|
| | Clay (SC-626GS) | Resin (A-15) | Y Zeolite | Y Zeolite |
| | Feed | | | |
| | Water Saturated | Water Saturated | Water Saturated | Dry |
| ACN breakthrough in initial bed (days) | immediate | 0.9 | immediate | 0.1 |
| ACN breakthrough in eighth bed (days) | 1.6 | 0.8 | 0.1 | 5.0 |
| NMP breakthrough in initial bed (days) | 6.9 | immediate | 0.1 | 0.1 |
| NMP breakthrough in eighth bed (days) | 30.6 | >15 | >7 | >8 |
| NFM breakthrough in initial bed (days) | 6.9 | immediate | 0.1 | 0.1 |
| NFM breakthrough in eighth bed (days) | >30 | 15.0 | 6.7 | 7.0 |

TABLE I-continued

| | Adsorbent | | | |
|---|---|---|---|---|
| | Clay (SC-626GS) | Resin (A-15) | Y Zeolite | Y Zeolite |
| | | Feed | | |
| | Water Saturated | Water Saturated | Water Saturated | Dry |
| Nitrogen on adsorbent (wt-%) | 1.3 | 1.4 | 0.9 | 0.8 |

Table I indicates that none of the beds under these conditions were effective to adsorb acetonitrile for a prolonged period. The Y zeolite may be effective to adequately adsorb acetonitrile from dry feed if a sufficiently large bed is utilized because break through in the initial bed was early, but reasonably prolonged in the eighth bed. Clay adsorbent seemed to be the most effective with NMP and NFM. Resin seemed to adequately adsorb NFM and NMP only if a sufficiently large bed of resin adsorbent is utilized because breakthrough of the initial bed was immediate but prolonged in the eighth bed.

Example III

A series of tests were conducted to evaluate the removal of acetonitrile (ACN) from benzene by contacting it with an adsorbent prepared by extruding approximately 80 wt-% Y-zeolite with about 20 wt-% alumina binder. The adsorbent had an ABD of 0.625 g/cc. For all tests, the adsorbent was dried at 120° C. for 2 hours prior to loading 25 grams of the adsorbent into a vessel. The tests were run at 24° C. and 150° C. operating temperatures and with varying amounts of water in the feed benzene.

Feedstock for the tests was prepared by spiking the benzene stream with ACN to give a target of approximately 20 wppm nitrogen. The starting benzene feed was dried before it was spiked with the ACN. In two of the tests, the benzene feed was spiked with water to determine the effect of water on the nitrogen adsorption. Results of spent adsorbent analysis for four tests are summarized in Table II.

TABLE II

| Test No. | Temperature (° C.) | Nominal Water Content (wppm) | Spent Adsorbent Average Nitrogen Content (wt-%) |
|---|---|---|---|
| 1 | 25 | 0 | 0.86 |
| 2 | 150 | 0 | 0.49 |
| 3 | 150 | 50 | 1.07 |
| 4 | 150 | 500 | 0.83 |

From Table II, it is evident that at elevated temperatures, in the range of 150° C., the addition of water to the feed improves the nitrogen capacity of the adsorbent. The test with 50 wppm water at 150° C. shows approximately 25% greater nitrogen capacity than the test at ambient temperature with no water in the benzene feed.

Example IV

The adsorbent from Test Nos. 2 and 3 in Example I were subjected to thermal gravimetric analysis (TGA) to determine the extent of coke accumulation on the adsorbents. The weight percent of coke deposited on the adsorbents and the temperature required to combust the coke from the adsorbents were estimated and shown in Table III.

TABLE III

| Test No. | Est. Coke Weight (wt-%) | Est. Combustion Temperature (° C.) |
|---|---|---|
| 2 | 8 | >400 |
| 3 | <1 | <400 |

Based on the TGA data, temperatures in excess of 400° C. were required to combust coke from the adsorbent from Test No. 2. Additionally, the coke level of adsorbent sample from Test No. 2, conducted at 150° C. and no water, is approximately 8 wt-%. Conversely, the adsorbent from Test No. 3 did not show a significant weight loss as the temperature increased above 400° C. It was estimated that the coke level of this adsorbent sample of Test No. 3, from the experiment conducted at 150° C. and 50 wppm water, is less than 1 wt-%. Therefore, addition of water has decreased the coke formation on the adsorbent by more than 85%. Regeneration of adsorbent will be less frequent when water is present during adsorption of nitrites at elevate temperatures.

What is claimed is:

1. A process for separating nitrile compounds from a hydrocarbon stream said process comprising:
   taking a contaminated hydrocarbon stream including water and organic nitrogen compounds including nitriles;
   contacting said hydrocarbon stream with an acidic, molecular sieve at a temperature of greater than 125° C.; and
   recovering a decontaminated hydrocarbon stream including a smaller concentration of nitriles than in said contaminated hydrocarbon stream.

2. The process of claim 1 wherein said molecular sieve is a zeolite.

3. The process of claim 2 wherein said acidic molecular sieve is a Y-zeolite.

4. The process of claim 1 wherein a concentration of water in said hydrocarbon stream is at least 50 wppm.

5. The process of claim 1 wherein a concentration of water in said hydrocarbon stream is stoichiometric with respect to the nitriles in the contaminated hydrocarbon stream.

6. The process of claim 1 wherein no more than 1 wt-% olefin is present in the contaminated hydrocarbon stream.

7. A process for separating nitrile compounds from a hydrocarbon stream, said process comprising:
   taking a contaminated hydrocarbon stream including water, organic nitrogen compounds including nitriles and no more than 1.0 wt-% olefins;
   contacting said hydrocarbon stream with an acidic zeolite at a temperature of greater than 125° C.; and
   recovering a decontaminated hydrocarbon stream including a smaller concentration of nitriles than in said contaminated hydrocarbon stream.

8. The process of claim 7 wherein said acidic zeolite is a Y-Zeolite or a Beta Zeolite.

9. The process of claim 7 wherein a concentration of water in said hydrocarbon stream is at least 20 wppm.

10. The process of claim 7 wherein a concentration of water in said hydrocarbon stream is at least 50 wppm.

11. The process of claim 7 wherein a concentration of water in said hydrocarbon stream is stoichiometric with respect to the nitriles in the contaminated hydrocarbon stream.

12. The process of claim 7 further including periodically combusting organic nitrogen compounds from said zeolite.

13. A process for separating nitriles from a hydrocarbon stream, said process comprising:
  taking a contaminated hydrocarbon stream including at least 50 wppm water and organic nitrogen compounds including nitriles;
  contacting said hydrocarbon stream with an acidic, molecular sieve at a temperature of greater than 125° C.; and
  recovering a decontaminated hydrocarbon stream including a smaller concentration of nitriles than in said contaminated hydrocarbon stream.

14. The process of claim 13 wherein said acidic, molecular sieve is a Y-Zeolite.

15. The process of claim 13 wherein a concentration of water in said contaminated hydrocarbon stream is stoichiometric with respect to the nitriles.

16. The process of claim 13 wherein said contaminated hydrocarbon stream includes no more than 1.0 wt-% olefins.

* * * * *